(12) United States Patent
Portney et al.

(10) Patent No.: US 7,238,201 B2
(45) Date of Patent: Jul. 3, 2007

(54) ACCOMMODATING INTRAOCULAR LENS SYSTEM WITH ENHANCED RANGE OF MOTION

(75) Inventors: Valdemar Portney, Tustin, CA (US); Nathaniel Gerald Portney, Irvine, CA (US)

(73) Assignee: Visiogen, Inc., Irvine, CA (US)

( * ) Notice: Subject to any disclaimer, the term of this patent is extended or adjusted under 35 U.S.C. 154(b) by 218 days.

(21) Appl. No.: 10/635,423

(22) Filed: Aug. 6, 2003

(65) Prior Publication Data

US 2004/0162612 A1  Aug. 19, 2004

Related U.S. Application Data

(60) Provisional application No. 60/447,260, filed on Feb. 13, 2003.

(51) Int. Cl.
*A61F 2/16* (2006.01)
(52) U.S. Cl. .................................. 623/6.34; 623/6.37
(58) Field of Classification Search ............... 623/6.34, 623/6.37
See application file for complete search history.

(56) References Cited

U.S. PATENT DOCUMENTS

| | | |
|---|---|---|
| 4,409,691 A | 10/1983 | Levy |
| 4,842,601 A | 6/1989 | Smith |
| 4,892,543 A | 1/1990 | Turley |
| 4,932,966 A | 6/1990 | Christie et al. |
| 4,963,148 A | 10/1990 | Sulc et al. |
| 4,994,082 A | 2/1991 | Richards et al. |
| 5,152,788 A | 10/1992 | Isaacson et al. |
| 5,275,623 A | 1/1994 | Sarfarazi |
| 5,354,335 A | 10/1994 | Lipshitz et al. |

(Continued)

FOREIGN PATENT DOCUMENTS

EP    0 337 390 A2    10/1989

(Continued)

OTHER PUBLICATIONS

John M. Ramocki et al., "Foldable Posterior Chamber Intraocular Lens Implantation in the Absence of Capsular and Zonular Support," *American Journal of Ophthalmolgoy*, vol. 127, pp. 213-216 (Feb. 1999).

(Continued)

*Primary Examiner*—David H. Willse
(74) *Attorney, Agent, or Firm*—Knobbe, Martens, Olson & Bear, LLP

(57) ABSTRACT

An intraocular lens system adapted to be implanted within an eye includes an anterior optic movable in a forward direction within the eye. The intraocular lens system further includes at least two anterior haptic arms, each anterior haptic arm having a first end coupled to the anterior optic and a second end adapted to be coupled to the eye. The intraocular lens system further includes a posterior optic movable in the forward direction within the eye and coupled to the anterior haptic arms. The intraocular lens system further includes at least one posterior haptic member adapted to be coupled to the eye and coupled to the posterior optic. The anterior haptic arms are responsive to a first forward movement of the posterior optic by actuating a second forward movement of the anterior optic substantially larger than the first forward movement.

12 Claims, 10 Drawing Sheets

U.S. PATENT DOCUMENTS

| | | | |
|---|---|---|---|
| 5,443,506 A | 8/1995 | Garabet | |
| 5,522,891 A | 6/1996 | Klaas | |
| 5,728,155 A | 3/1998 | Anello et al. | |
| 5,968,094 A | 10/1999 | Werblin et al. | |
| 5,984,962 A | 11/1999 | Anello et al. | |
| 6,197,058 B1 | 3/2001 | Portney | |
| 6,231,603 B1 | 5/2001 | Lang et al. | |
| 6,280,471 B1 | 8/2001 | Peyman et al. | |
| 6,423,094 B1 | 7/2002 | Sarfarazi | |
| 6,488,708 B2 | 12/2002 | Sarfarazi | |
| 6,503,276 B2 | 1/2003 | Lang et al. | |
| 6,599,317 B1 * | 7/2003 | Weinschen et al. | 623/6.34 |
| 6,616,691 B1 | 9/2003 | Tran | |
| 6,645,246 B1 * | 11/2003 | Weinschenk et al. | 623/6.37 |
| 2001/0001836 A1 | 5/2001 | Cumming | |
| 2001/0012964 A1 | 8/2001 | Lang et al. | |
| 2002/0068971 A1 | 6/2002 | Cumming | |
| 2002/0072795 A1 | 6/2002 | Green | |
| 2002/0116060 A1 | 8/2002 | Nguyen et al. | |
| 2002/0143395 A1 | 10/2002 | Skottun | |
| 2002/0188351 A1 | 12/2002 | Laguette | |
| 2002/0193876 A1 | 12/2002 | Lang et al. | |
| 2003/0109925 A1 | 6/2003 | Ghazizadeh et al. | |

FOREIGN PATENT DOCUMENTS

| | | |
|---|---|---|
| WO | WO 84/04449 | 11/1984 |
| WO | WO 96/15734 | 5/1996 |
| WO | WO 99/20206 | 4/1999 |
| WO | WO 00/27315 | 5/2000 |
| WO | WO 00/61036 | 10/2000 |
| WO | WO 00/66037 | 11/2000 |
| WO | WO 01/34067 | 5/2001 |
| WO | WO 02/071983 A1 | 9/2002 |
| WO | WO 03/092552 A1 | 11/2003 |
| WO | PCT/US2004/003851 | 2/2004 |

OTHER PUBLICATIONS

Rana Altan-Yaycioglu et al., "Pseudo-accommodation with Intraocular Lenses Implanted in the Bag," *Journal of Refractive Surgery*, vol. 18, pp. 271-275 (May/Jun. 2002).

Michael Küchle et al., "Implantation of a New Accommodative Posterior Chamber Intraocular Lens," *Journal of Refractive Surgery*, vol. 18, pp. 208-216, (May/Jun. 2002).

Tsutomu Hara et al., "Accommodative Intraocular Lens with Spring Action Part 1. Design and Placemnent in an Excised Animal Eye," *Ophthalmic Surgery*, vol. 21, pp. 128-133 (Feb. 1990).

* cited by examiner

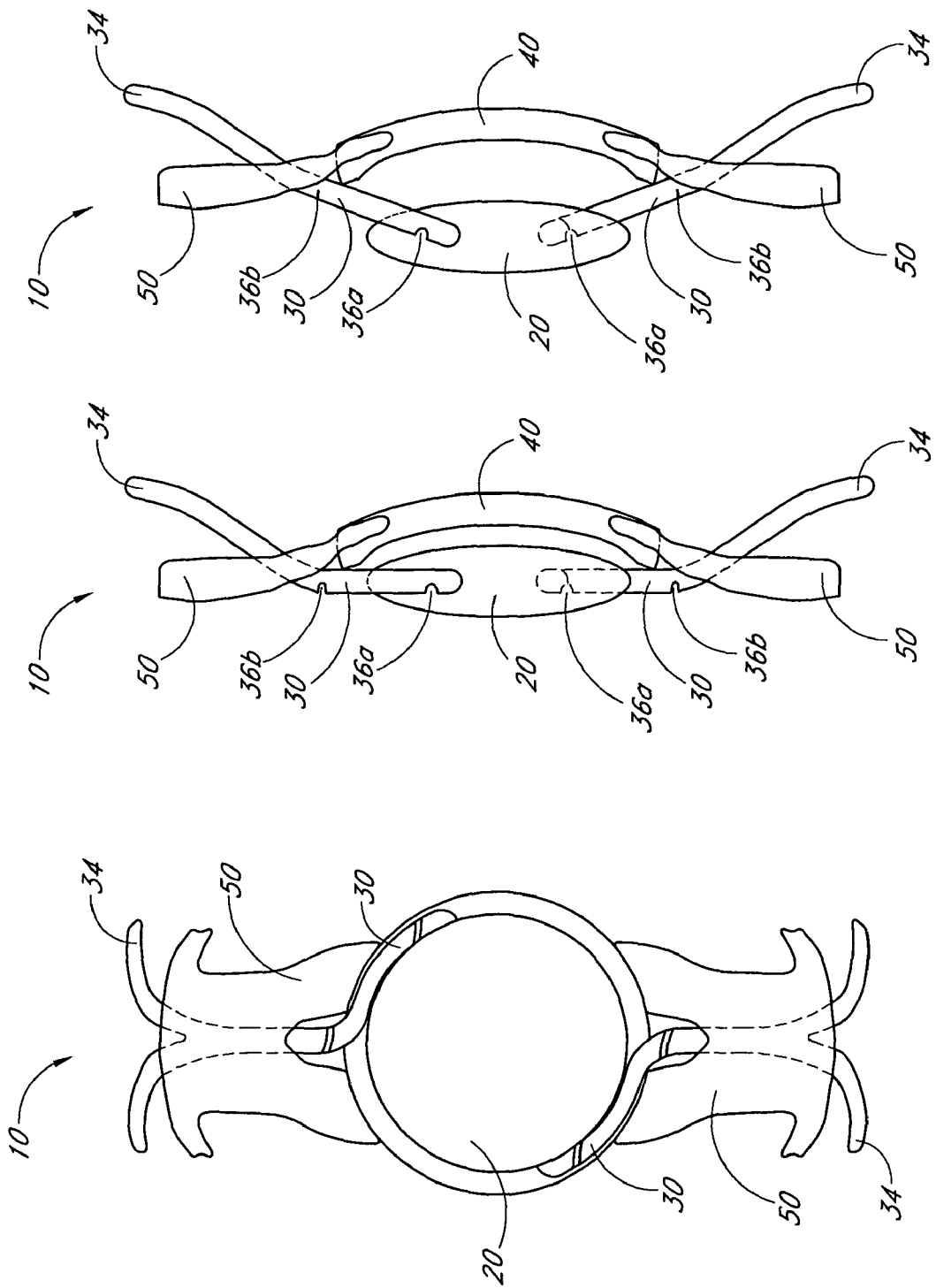

ACCOMMODATING INTRAOCULAR LENS SYSTEM WITH ENHANCED RANGE OF MOTION

CLAIM OF PRIORITY

This application claims benefit under 35 U.S.C. § 119(e) to U.S. Provisional Application No. 60/447,260, filed Feb. 13, 2003, which is incorporated in its entirety by reference herein.

BACKGROUND OF THE INVENTION

1. Field of the Invention

The present invention relates generally to intraocular lens systems, and more particularly to accommodating intraocular lens systems.

2. Description of the Related Art

The ability of the eye to modify its refractive power for viewing objects of varying distances is termed "accommodation." Upon relaxation of the ciliary muscle, the zonular fibers, which connect the capsular bag of the lens to the ciliary muscle, pull on the capsular bag around its equator, causing the entire lens to become less convex (i.e., flatten), so that the lens can focus light from objects at a distance. Similarly, contraction of the ciliary muscle (i.e., reduction of the circumference of the ciliary muscle) results in relaxation of the zonular fibers. Correspondingly, the lens equatorial diameter decreases, the lens central thickness increases, and the lens becomes more spherical with an increased curvature of the anterior and posterior lens surfaces. These changes of the shape of the lens result in accommodation by increasing the dioptric power of the lens so as to focus light from nearer objects onto the retina.

Synthetic intraocular lenses implanted in patients for the treatment of cataracts typically do not have the ability to change shape as do natural lenses. Therefore, such patients experienced a degradation of their ability to accommodate. Efforts to develop intraocular lens systems which provide some degree of accommodation have included single optic intraocular lens systems and dual optic intraocular lens systems.

SUMMARY OF THE INVENTION

Certain embodiments of the present invention provide an intraocular lens system adapted to be implanted within an eye. The intraocular lens system comprises an anterior optic movable in a forward direction within the eye. The intraocular lens system further comprises at least two anterior haptic arms, each anterior haptic arm having a first end coupled to the anterior optic and a second end adapted to be coupled to the eye. The intraocular lens system further comprises a posterior optic movable in the forward direction within the eye and coupled to the anterior haptic arms. The intraocular lens system further comprises at least one posterior haptic member adapted to be coupled to the eye and coupled to the posterior optic. The anterior haptic arms are responsive to a first forward movement of the posterior optic by actuating a second forward movement of the anterior optic substantially larger than the first forward movement.

Certain other embodiments provide an intraocular lens system comprising a posterior optic adapted to move a first distance in a forward direction. The intraocular lens system further comprises an anterior optic coupled to the posterior optic and adapted to move a second distance in the forward direction in response to the first distance movement of the posterior optic, wherein the second distance is larger than the first distance.

Certain other embodiments provide an intraocular lens system comprising a posterior optic adapted to move a first distance in a forward direction. The intraocular lens system further comprises an anterior optic adapted to move a second distance in the forward direction, wherein the second distance is larger than the first distance.

Certain other embodiments provide a method of facilitating accommodative motion in an intraocular lens system. The method comprises translating forward movement of a posterior optic of the intraocular lens system into forward movement of an anterior optic of the intraocular lens system, thereby providing ocular accommodation.

For purposes of summarizing the present invention, certain aspects, advantages and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 5A–5C schematically illustrate another embodiment of the intraocular lens system in which the second end of each anterior haptic arm is coupled to the ocular structure substantially independently from the posterior haptic members.

DETAILED DESCRIPTION OF THE PREFERRED EMBODIMENT

Previous designs of dual optic intraocular lens systems replace the natural lens with an anterior optic and a posterior optic, coupled together by a spring mechanism and implanted within the capsular bag. Such dual optic intraocular lens systems depend on the interaction of the optics with the capsular bag. When the ciliary muscle is relaxed and the zonular fibers are under tension, the capsular bag is pulled at its equator and stretched, thereby bringing the anterior optic and the posterior optic closer together and compressing the spring mechanism. When the ciliary muscle is contracted and the zonular fibers are relaxed, the capsular bag relaxes and the spring mechanism pushes the anterior optic and the posterior optic apart to their equilibrium positions. These relative movements of the anterior and posterior optics provide some measure of accommodation. Such dual optic intraocular lens systems are typically designed to have a high power anterior lens and a combined dioptric power to attempt to achieve a significant accommodation range of several dioptric powers over the range of spacings between the anterior optic and the posterior optic.

There are several drawbacks of such dual optic intraocular lens systems which rely on the interaction of the ocular elements with the capsular bag to provide accommodation. The mechanical properties of the capsular bag are likely to vary with individual, age, and the surgical implantation procedure used, thereby making it a challenge to predict an accommodating outcome for such dual optic intraocular lens systems. Another drawback of such dual optic intraocular lens systems relates to the fact that, unlike for natural lenses, the relaxed state of the system has the two optics spaced apart (i.e., in the near power configuration). The performance of such dual optic intraocular lens systems depends upon the ability of the capsular bag to bring the anterior optic to the specifically designed position close to the posterior optic. The variability of the behavior of the capsular bag therefore results in an inherent variability of the degree of emmetropia achieved by the dual optic intraocular lens system.

Embodiments of the apparatus and method disclosed herein offer a significant improvement over the current dual optic intraocular lens systems by amplifying a limited forward (i.e., in the anterior direction) movement of the posterior optic into a larger forward movement of the high power anterior optic. Accordingly, certain embodiments disclosed herein utilize movement of the high power anterior optic to achieve practical accommodation without the corresponding reliance on the mechanical properties of the capsular bag. As a further advantage, certain embodiments disclosed herein have an emmetropic relaxed state, thereby making the ability of the intraocular lens system to achieve emmetropia substantially independent from the accommodating characteristics of the system.

Figure 1B:
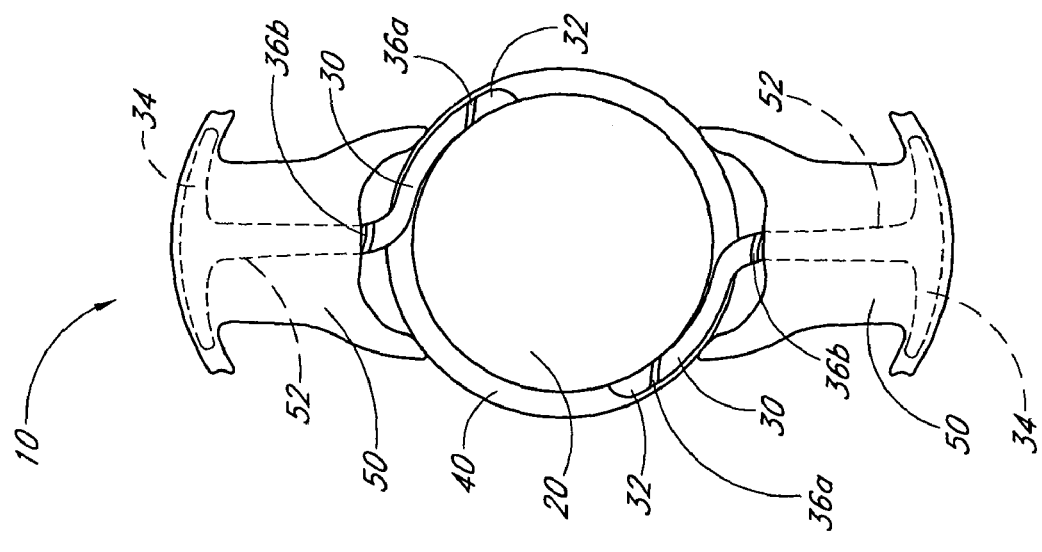
FIGS. 1A and 1B schematically illustrate a dual optic intraocular lens system in accordance with embodiments described herein.
Figure 1A:
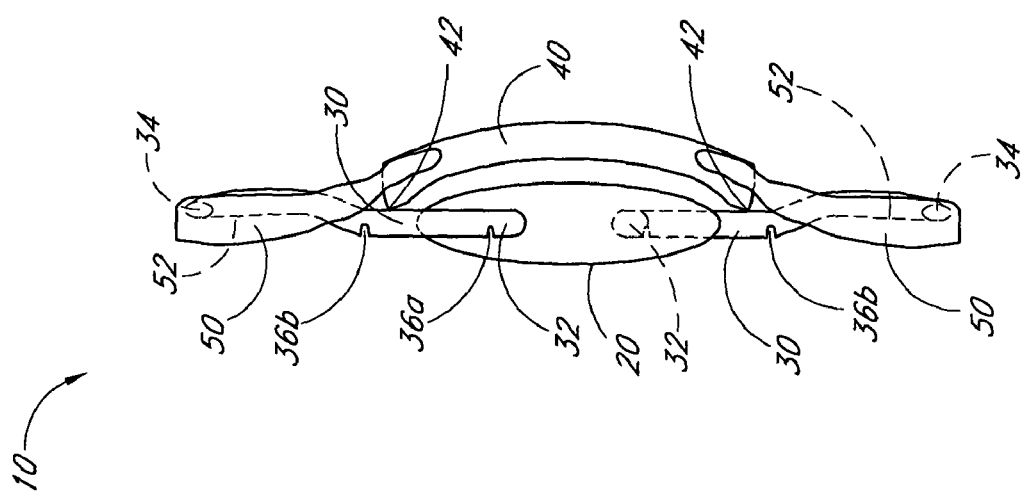

FIGS. 1A and 1B schematically illustrate an intraocular lens system 10 adapted to be implanted within an eye in accordance with embodiments described herein. The intraocular lens system 10 comprises an anterior optic 20 movable in a forward direction within the eye. The intraocular lens system 10 further comprises at least two anterior haptic arms 30. Each anterior haptic arm 30 has a first end 32 coupled to the anterior optic 20 and a second end 34 adapted to be coupled to the eye. The intraocular lens system 10 further comprises a posterior optic 40 movable in the forward direction within the eye and coupled to the anterior haptic arms 30. The intraocular lens system 10 further comprises at least one posterior haptic member 50 adapted to be coupled to the eye and coupled to the posterior optic 40. The anterior haptic arms 30 are responsive to a first forward movement of the posterior optic 40 by actuating a second forward movement of the anterior optic 20. The second forward movement is substantially larger than the first forward movement.

In certain embodiments, the anterior optic 20 comprises a substantially transparent biocompatible material. Examples of suitable materials include, but are not limited to, PMMA, silicone, and acrylic. As schematically illustrated in FIGS. 1A and 1B, the anterior optic 20 is circular in certain embodiments and has two convex surfaces through which the light propagates. Other shapes and surface contours of the anterior optic 20 are compatible with embodiments described herein. The anterior optic 20 has a relatively high power in certain embodiments, and has a power of at least approximately 30 diopters in other embodiments.

In certain embodiments, the anterior haptic arms 30 comprise a biocompatible material. Examples of suitable materials include, but are not limited to, PMMA, Nitinol, and other biocompatible plastics and metals. The anterior haptic arms 30 and the anterior optic 20 can be formed as a single unit, and for certain such embodiments, the same materials can be used for the anterior haptic arms 30 and the anterior optic 20. In other embodiments, the first end 32 of each anterior haptic arm 30 is mechanically coupled to the anterior optic 20, with exemplary couplings including, but not limited to, glue, pressure, mating post and hole assemblies and interlocking assemblies.

In certain embodiments, the second end 34 of each anterior haptic arm 30 is adapted to be coupled to the eye by placement within the capsular bag. This configuration can be accomplished by making the overall length of the assembly of the anterior optic 20 and the anterior haptic arms 30 approximately equal to the diameter of the capsular bag, which can range from approximately 9 millimeters to approximately 11 millimeters. In certain such embodiments, the overall length between the second ends 34 of the two anterior haptic arms 30 of FIGS. 1A and 1B is approximately 10.5 millimeters.

In other embodiments, the second end 34 of each anterior haptic arm 30 is adapted to be coupled to other structures of the eye (e.g., the zonular fibers or the ciliary body). Such embodiments can be advantageously used in circumstances in which the capsular bag is absent, or in which the capsular bag is not in the optimal position for the intraocular lens system 10. Certain such embodiments have an overall length of the assembly of the anterior optic 20 and the anterior haptic arms 30 greater than approximately 11 millimeters, while other embodiments have an overall length of this assembly of approximately 13 millimeters.

As described more fully below, the anterior haptic arms 30 of certain embodiments provide sufficient flexibility for substantial forward movement of the anterior optic 20. Sufficient flexibility can be provided by using a shape-memory alloy, such as Nitinol, for the anterior haptic arms 30. Each anterior haptic arm 30 can also comprise one or more notches (shown in FIGS. 1A and 1B as notches 36a, 36b) for areas of flexure which provide additional flexibility to the anterior haptic arm 30 and reduced resistance to the desired movements.

In certain embodiments, the posterior optic 40 comprises a substantially transparent biocompatible material. Examples of suitable materials include, but are not limited to, PMMA, silicone, and acrylic. As schematically illustrated in FIGS. 1A and 1B, the posterior optic 40 of certain embodiments is circular and with a meniscus shape (i.e., has one convex surface and one concave surface through which the light propagates). Other shapes and surface contours of the posterior optic 40 are compatible with embodiments described herein. The posterior optic 40 of certain embodiments is dispersive (i.e., has a negative diopter power), and in other embodiments has a power of at least approximately −10 diopters.

In certain embodiments, the posterior haptic member 50 comprises a biocompatible material. Examples of suitable materials include, but are not limited to, PMMA, Nitinol, and other biocompatible plastics and metals. The posterior haptic member 50 and the posterior optic 40 are formed as a single unit in certain embodiments, and the same materials can be used for the posterior haptic member 50 and the posterior optic 40. In other embodiments, the posterior haptic member 50 is mechanically coupled to the posterior optic 40, with exemplary couplings including, but not limited to, glue,. pressure, mating post and hole assemblies, and interlocking assemblies. In certain embodiments, the coupling between the posterior haptic member 50 and the posterior optic 40 is a flexible connection which allows easier and substantial movement of the posterior optic 40 in the forward direction, as compared to a fixed haptic coupling. In the embodiment illustrated in FIGS. 1A and 1B, the intraocular lens system 10 comprises a pair of posterior haptic members 50 positioned substantially symmetrically to the posterior optic 40.

In certain embodiments, each posterior haptic member 50 is adapted to be coupled to the eye by placement within the capsular bag. This configuration can be accomplished by making the overall length of the assembly of the posterior optic 40 and the posterior haptic members 50 approximately equal to the diameter of the capsular bag, which can range from approximately 9 millimeters to approximately 11 millimeters. In certain such embodiments, the overall length of the assembly of the posterior optic 40 and the posterior haptic members 50 of FIGS. 1A and 1B is approximately 10.5 millimeters.

In other embodiments, each posterior haptic member 50 is coupled to other structures of the eye (e.g., the zonular fibers or the ciliary body). Such embodiments can be advantageously used in circumstances in which the capsular bag is absent, or in which the capsular bag is not in the optimal position for the intraocular lens system 10. Certain such embodiments have an overall length of the assembly of the posterior optic 40 and the anterior haptic members 50 greater than approximately 11 millimeters, while other embodiments have an overall length of this assembly of approximately 13 millimeters.

In certain embodiments, the posterior haptic members 50 are fixedly coupled to the second ends 34 of the anterior haptic arms 30. In such embodiments, coupling the posterior haptic member 50 to the eye thereby couples the second end 34 of the anterior haptic arm 30 to the eye. For example, the second end 34 of the anterior haptic arm 30 can be imbedded at various locations within the posterior haptic member 50. FIGS. 1A and 1B schematically illustrate one such embodiment in which each posterior haptic member 50 has a cut-out portion 52 near the periphery of the posterior haptic member 50 within which the second end 34 of an anterior haptic arm 30 is placed. Other embodiments can have the anterior haptic arm 30 imbedded at other locations within the posterior haptic member 50. Still other embodiments can have the posterior haptic member 50 imbedded within the anterior haptic arm 30.

In certain embodiments, the posterior optic 40 is coupled to the anterior haptic arms 30 such that forward movement of the posterior optic 40, ostensibly in response to the vitreous pressure of the posterior chamber, moves the anterior haptic arms 30 in the forward direction. In the embodiment schematically illustrated in FIGS. 1A and 1B, the posterior optic 40 comprises an edge 42 which contacts, or otherwise engages, at least one of the anterior haptic arms 30. In certain embodiments, the edge 42 extends completely around the circumference of the posterior optic 40, while in other embodiments, the edge 42 exists only at portions of the circumference in proximity to the anterior haptic arms 30.

Figure 2B:
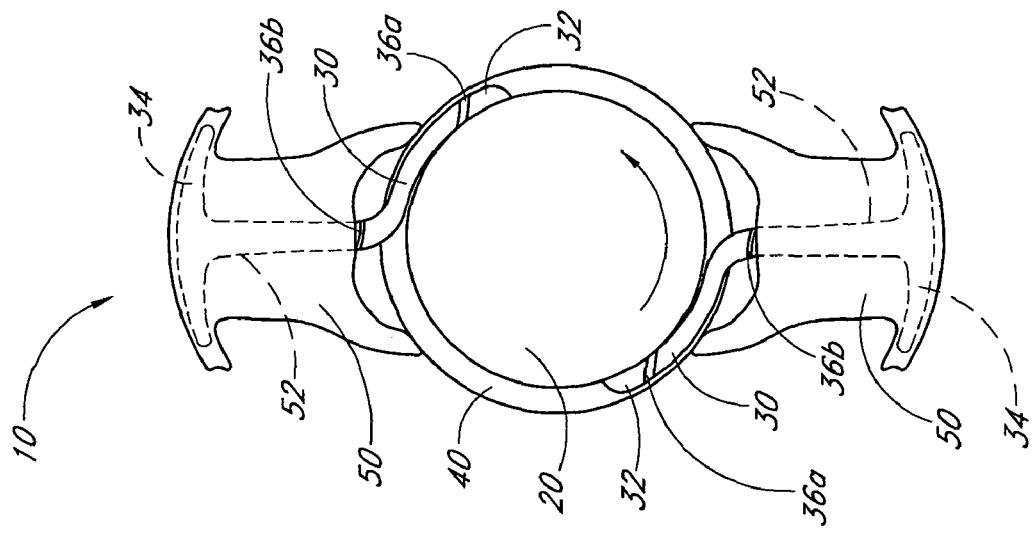
FIGS. 2A and 2B schematically illustrate the dual optic intraocular lens system of FIGS. 1A and 1B upon forward movement of the posterior optic.
Figure 2A:
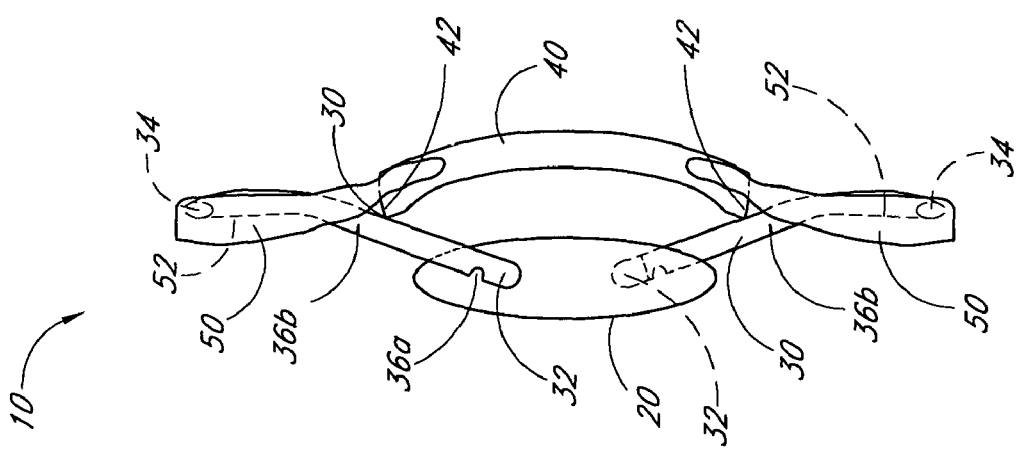
Figure 4B:
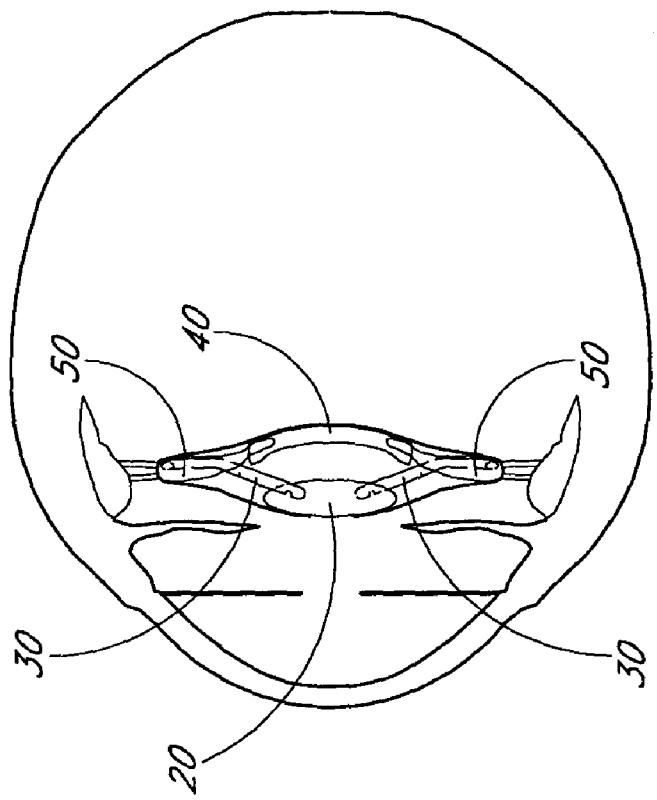
FIGS. 4A and 4B schematically illustrate an embodiment of the intraocular lens system within the eye.

FIGS. 2A and 2B schematically illustrate the effects of forward movement of the posterior optic 40 in the intraocular lens system 10 of FIGS. 1A and 1B. As shown by FIG. 2A, the periphery of each posterior haptic member 50 remains relatively stationary while the posterior optic 40 moves forward. By moving forward, the edge 42 of the posterior optic 40 deflects the anterior haptic arms 30 in the forward direction. This deflection of the anterior haptic arms 30 moves the anterior optic 20 in the forward direction. Compression of the notch 36a and expansion of the notch 36b both contribute to the flexibility of the anterior haptic arm 30 and facilitate the forward movement of the anterior optic 20. As shown in FIG. 4B, the anterior optic 40 rotates slightly in response to the forward movement due to the foreshortening of the projection of the anterior haptic arms 30 in the plane of the second ends 34 of the anterior haptic arms 30.

Relatively small movements of the posterior optic 40 can yield relatively significant movements of the anterior optic 20. Comparing the equilibrium configuration illustrated by FIG. 1A with the displaced configuration illustrated by FIG. 2A, the posterior optic 40 is displaced by only a small amount in the forward direction, but the anterior optic 20 is displaced by a larger amount in the forward direction.

Figure 3B:
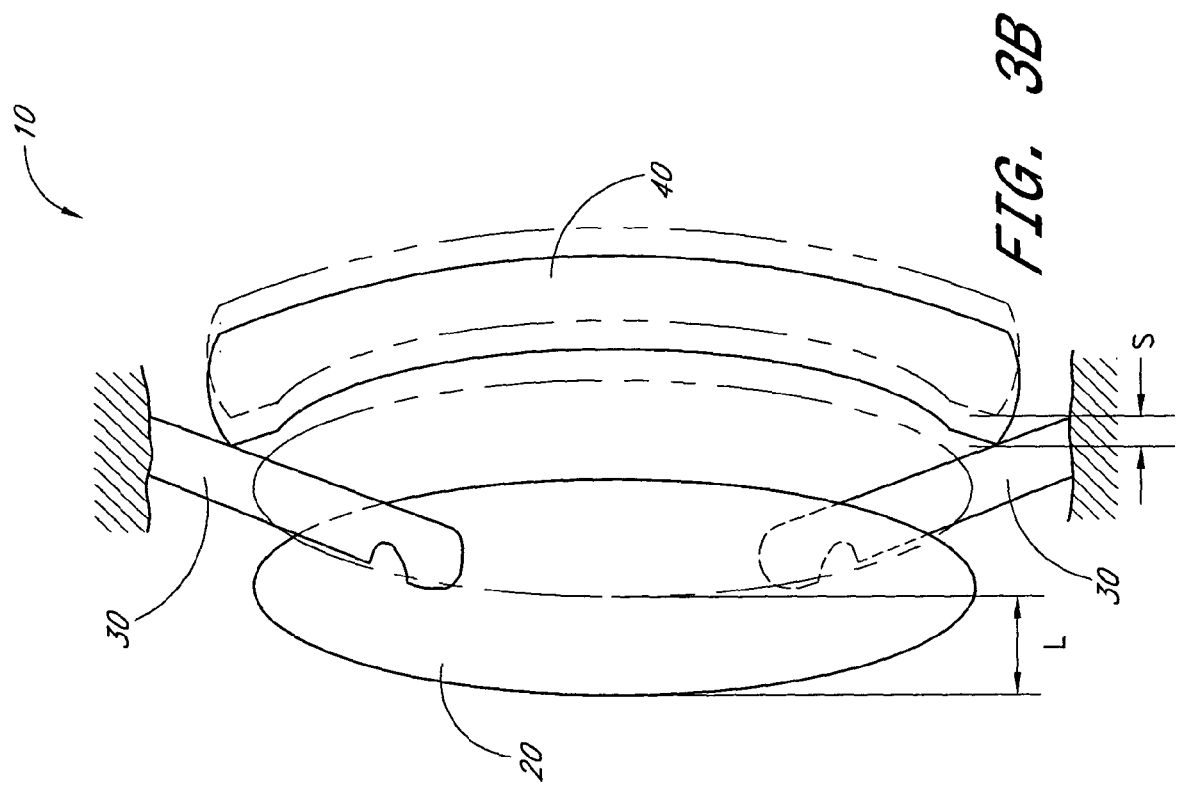
FIGS. 3A–3C schematically illustrate a simplified model of the intraocular lens system to demonstrate the amplification of the displacement of the anterior optic.
Figure 3A:
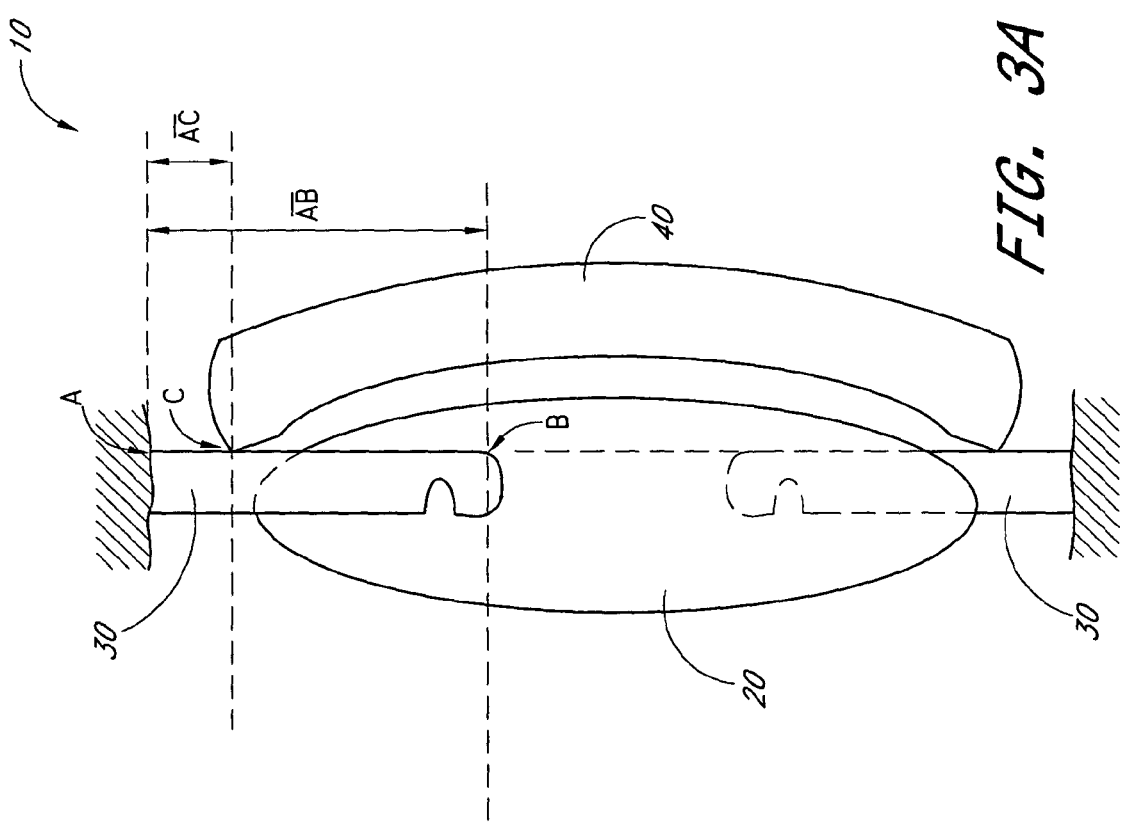
Figure 3C:
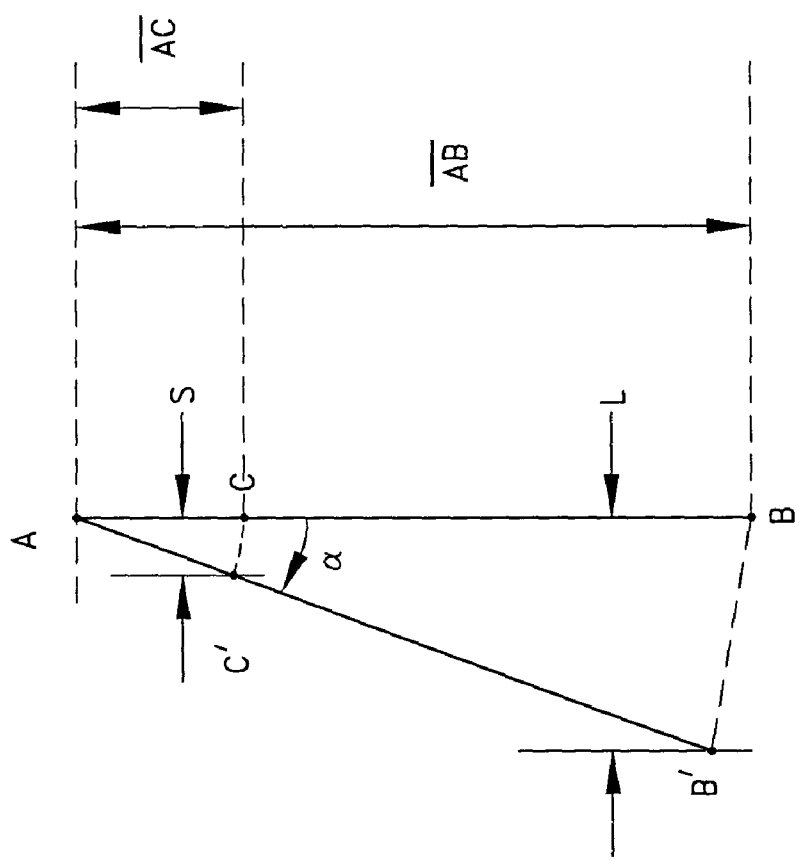

FIGS. 3A–3C schematically illustrate a simplified model of the intraocular lens system 10 to demonstrate this amplification of the displacement of the anterior optic 20. FIG. 3A schematically illustrates the anterior optic 20, the anterior haptic arms 30, and the posterior optic 40 in their equilibrium positions, and FIG. 3B schematically illustrates these components in their displaced positions due to contraction of the ciliary muscle. In FIGS. 3A and 3B, the movement of each anterior haptic arm 30 in response to the movement of the posterior optic 40 is modeled as a rotation about a point A.

In the equilibrium configuration of the intraocular lens system 10 shown in FIG. 3A, the anterior optic 20 and the posterior optic 40 are spaced relatively close together and the anterior haptic arms 30 are in a relaxed (i.e., non-flexed) position. Each anterior haptic arm 30 is modeled as coupling to the anterior optic 20 at a point B, and the edge 42 of the posterior optic 40 is modeled as contacting each anterior haptic arm 30 at a point C.

In the displaced configuration of the intraocular lens system 10, as shown in FIG. 3B, the posterior optic 40 has moved in the forward direction, pushing the anterior haptic arms 30 so that the point of contact is at the point C' and the point of coupling of the anterior haptic arm 30 with the anterior optic 20 is at the point B'. Each anterior haptic arm 30 has rotated about the point A by an angle α, acting as a lever in amplifying the forward movement of the posterior optic 40 into a larger forward movement of the anterior optic 20.

FIG. 3C schematically illustrates the geometry of the intraocular lens system 10. For a forward movement of the posterior optic 40 given by the line CC', the anterior optic 20 undergoes a forward movement given by the projection of the line BB' in the forward direction. For small angles α (where the projection of the line BB' along the forward direction is approximately equal to the line BB'), the relation between the movement (CC') of the posterior optic 40 and the movement (BB') of the anterior optic 20 is determined by the ratios of the moments along the anterior haptic arms 30 and can be expressed as:

$$BB' = mCC' = \left(\frac{AB}{AC}\right)CC',$$

where m is the movement amplification factor. Thus, depending on the contact position of the edge 42 of the posterior optic 40 with the anterior haptic arm 30, the forward movement of the posterior optic 40 can be amplified by a factor of between approximately 2 and approximately 4 in certain embodiments, and by a factor higher than 4 in other embodiments. For example, for movements of the posterior optic 40 of approximately 0.35 millimeters and a movement amplification factor of approximately 3, a forward movement of the anterior optic 20 of approximately one millimeter can be achieved. For an anterior optic 20 with a power of approximately 30 diopters, this movement of the anterior optic 20 can yield approximately 2 diopters of accommodation. In certain embodiments, the forward movement of the posterior optic 40 is between approximately 0.3 millimeters and approximately 0.5 millimeters.

Figure 4A:
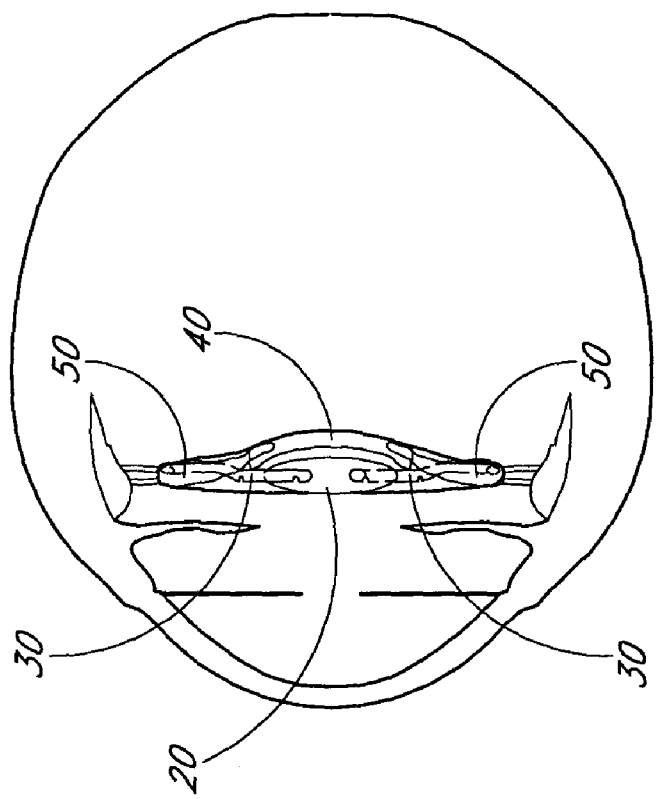

FIGS. 4A and 4B schematically illustrate an embodiment of the intraocular lens system 10 within the capsular bag of the eye. FIG. 4A depicts an unaccommodating state in which the ciliary muscle is relaxed and the anterior optic 20 is in proximity to the posterior optic 40. FIG. 4B depicts an accommodating state in which the ciliary muscle is contracted, moving the posterior optic 40 in the forward direction by a first distance. The anterior optic 20 has responded to the movement of the posterior optic 40 by moving forward by a second distance larger than the first distance, thereby producing a significant accommodating effect. In certain embodiments, as illustrated in FIGS. 4A and 4B, the equatorial diameter of the anterior optic 20 is larger than the capsularhexis diameter so that the capsular bag overlaps the periphery of the anterior optic 20, in a manner similar to that of conventional lens implantations. In certain other embodiments, the capsularhexis diameter is larger than the equatorial diameter of the anterior optic 20 in order to allow the anterior optic 20 to move substantially unobstructed by the capsular bag.

FIGS. 5A–5C schematically illustrate another embodiment of the intraocular lens system 10 in which the second end 34 of each anterior haptic arm 30 is coupled to the ocular structure (e.g., the capsular bag) substantially independently from the posterior haptic members 50. Each anterior haptic arm 30 is uncoupled from the posterior haptic members 50 or only loosely coupled to one of the posterior haptic members 50, such that the posterior haptic members 50 can move substantially independently from the anterior haptic arms 30. In the embodiment illustrated in FIGS. 5A–5C, the second end 34 of each anterior haptic arm 30 is flexible and splayed in a "Y"-shape which fits within the capsular bag. Such embodiments provide a flexible anchoring of the anterior haptic arm 30 to the capsular bag.

FIGS. 5B and 5C show the intraocular lens system 10 in an unaccommodating state and an accommodating state, respectively. In the unaccommodating state of FIG. 5B, the anterior optic 20 and the posterior optic 40 are in proximity to one another. In certain embodiments, in the accommodating state, the posterior optic 40 and the posterior haptic members 50 have jointly moved forward, deflecting the anterior haptic arms 30, and moving the anterior optic 20 forward, thereby increasing the spacing between the anterior optic 20 and the posterior optic 40. In such embodiments, flexibility of the coupling between the posterior haptic members 50 and the posterior optic 40 is not critical since the posterior haptic members 50 move jointly with the posterior optic 40 during accommodation. In other embodiments, the anterior haptic arms 30 are rotatably connected to the posterior haptic members 50 at pivots. In such embodiments, each anterior haptic arm 30 rotates about the pivot upon translations of the posterior haptic member 50, thereby moving the anterior optic 20 forward by a scissor-like action.

In certain embodiments, the edge-to-edge length of the anterior haptic arms 30 is larger than the edge-to-edge length of the posterior haptic members 50. The edge-to-edge length of the posterior haptic members 50 is sufficiently short in certain embodiments to be uncoupled or loosely coupled to the eye, so as to allow free forward movement of the posterior haptic members 50 together with the posterior optic 40 itself. The edge-to-edge length of the posterior haptic members 50 of certain embodiments is between approximately 8 millimeters and approximately 10.5 millimeters, and is equal to approximately 9.7 millimeters in other embodiments.

Figure 6B:
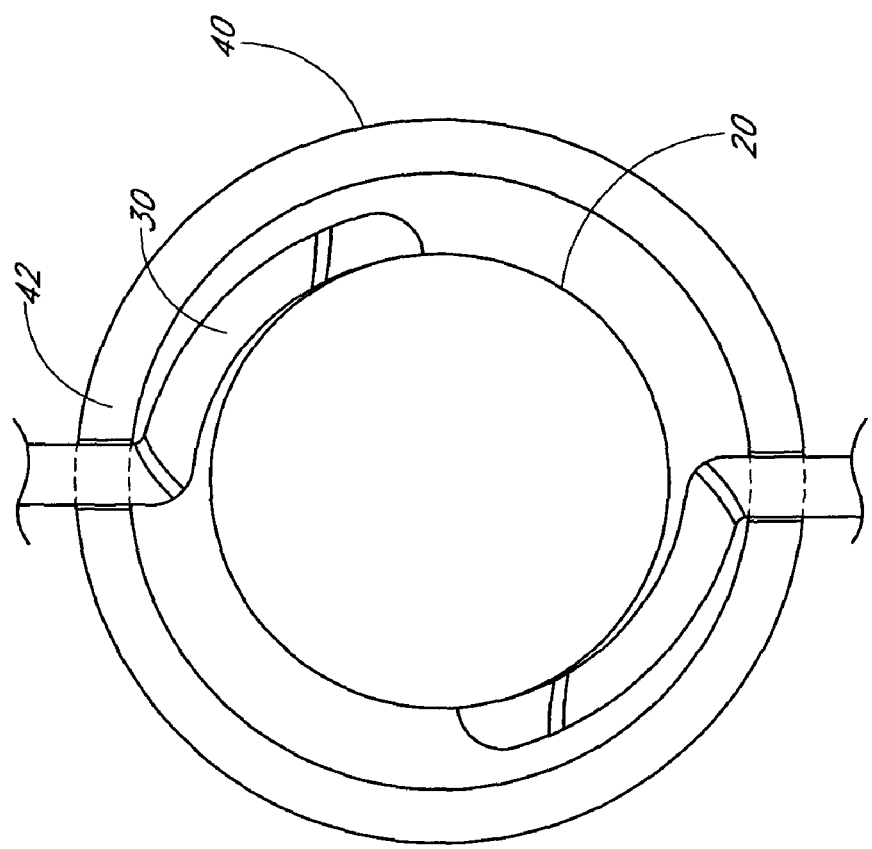
FIGS. 6A and 6B schematically illustrate an embodiment utilizing a slit in the edge of the posterior optic.
Figure 6A:
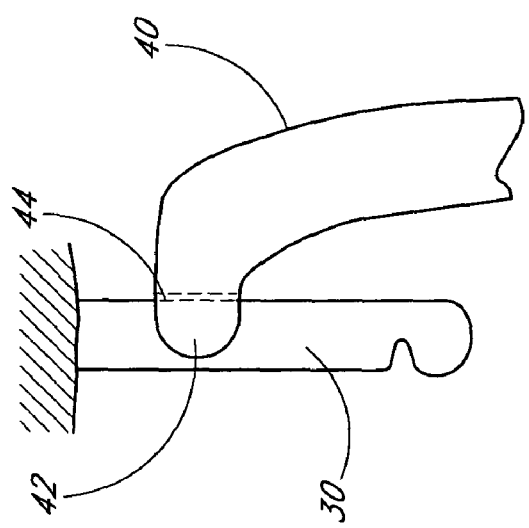

FIGS. 6A and 6B schematically illustrate an embodiment utilizing a groove 44 in the edge 42 of the posterior optic 40. The groove 44 is adapted to engage an anterior haptic arm 30 and to constrain the anterior haptic arm 30 to move primarily along one direction while remaining in the groove 44. The groove 44 thereby provides a coupling between the posterior optic 40 and the anterior haptic arm 30 which is constrained from slipping along the direction perpendicular to the anterior haptic arm 30. Similarly in other embodiments, constraint of the motion of the anterior haptic arm 30 can be achieved using other recesses, protrusions, or other structures on or in proximity to the posterior optic 40.

Figure 7:
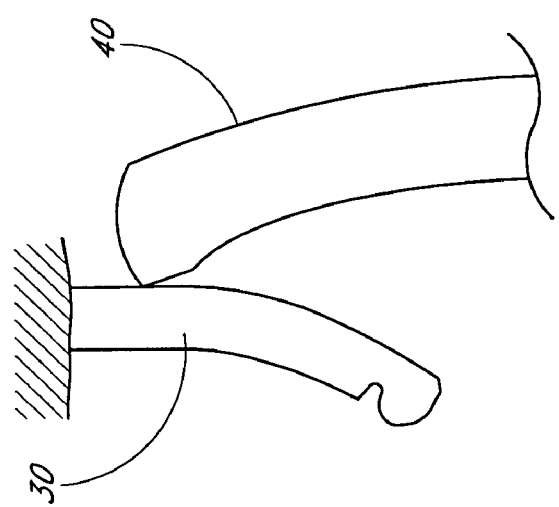
FIG. 7 schematically illustrates an embodiment utilizing an anterior haptic arm which is curved in the forward direction.

FIG. 7 schematically illustrates an embodiment utilizing an anterior haptic arm 30 which is curved in the forward direction. The curvature of the anterior haptic arm 30 can serve to increase the magnitude of the movement of the anterior optic 20. In addition, the curvature of the anterior haptic arm 30 can serve to increase the distance between the anterior optic 20 and the posterior optic 40 when in the unaccommodating state as compared to embodiments with uncurved anterior haptic arms 30. In certain embodiments, the curvature of the anterior haptic arm 30 can also serve as a cam to provide nonuniform movement of the anterior optic 20 in response to movement of the posterior optic 40.

Figure 8:
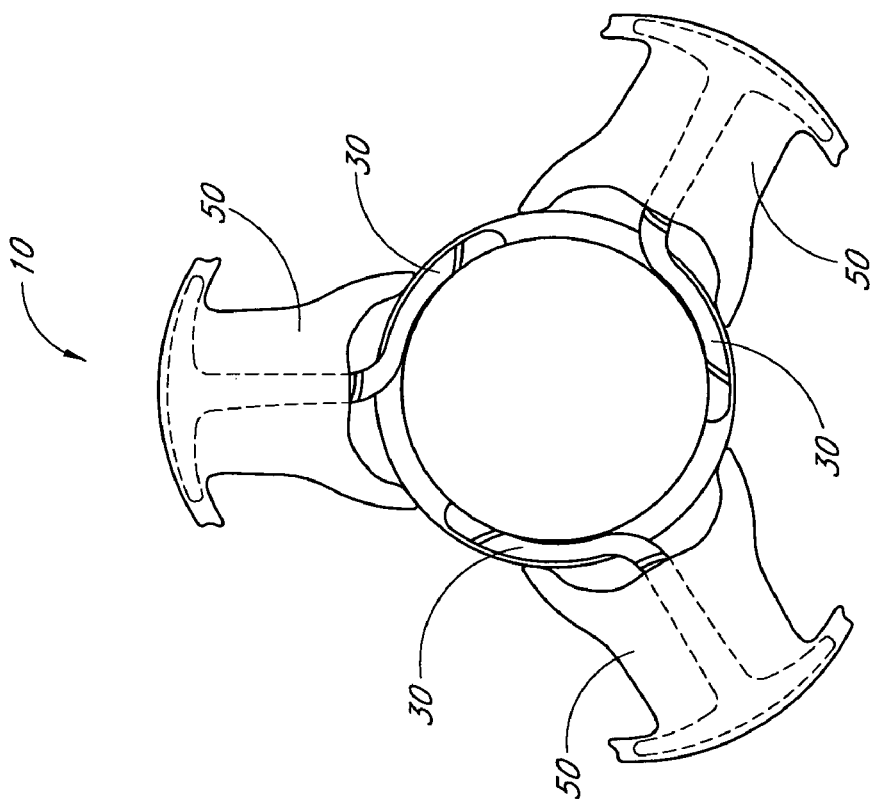
FIG. 8 schematically illustrates an embodiment which utilizes three pairs of anterior haptic arms and posterior haptic members.

FIG. 8 schematically illustrates an embodiment utilizing three pairs of anterior haptic arms 30 and posterior haptic members 50. Such embodiments can provide additional stability of the intraocular lens system 10 within the eye. Other embodiments can use still more anterior haptic arms 30 and posterior haptic members 50.

Figure 9:
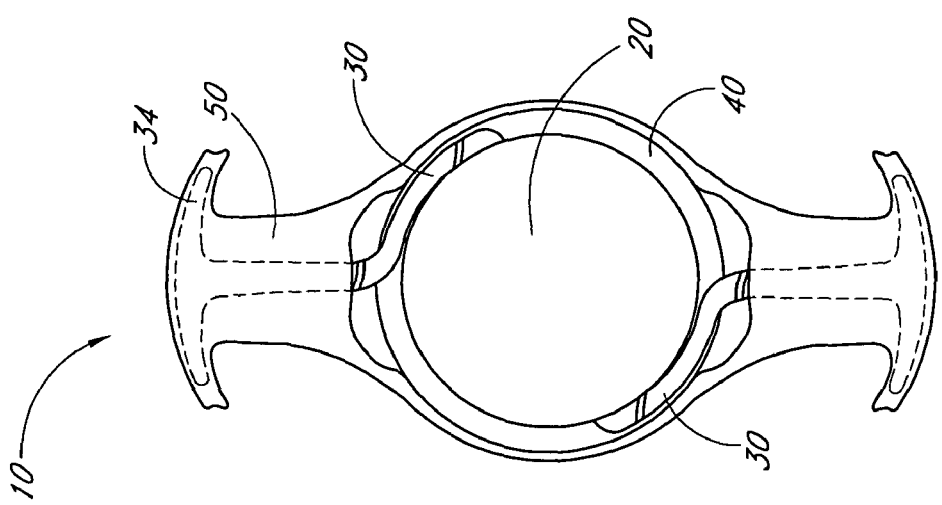
FIG. 9 schematically illustrates an embodiment of the intraocular lens system utilizing a single posterior haptic member.

FIG. 9 schematically illustrates an embodiment of the intraocular lens system 10 utilizing a single posterior haptic member 50. In certain such embodiments in which the posterior haptic member 50 is coupled to the eye, the posterior haptic member 50 is flexibly coupled to the posterior optic 40. In other embodiments in which the posterior haptic member 50 is uncoupled or loosely coupled to the eye so that they can move together, the coupling between the posterior haptic member 50 and the posterior optic 40 is nonflexible.

Figure 10:
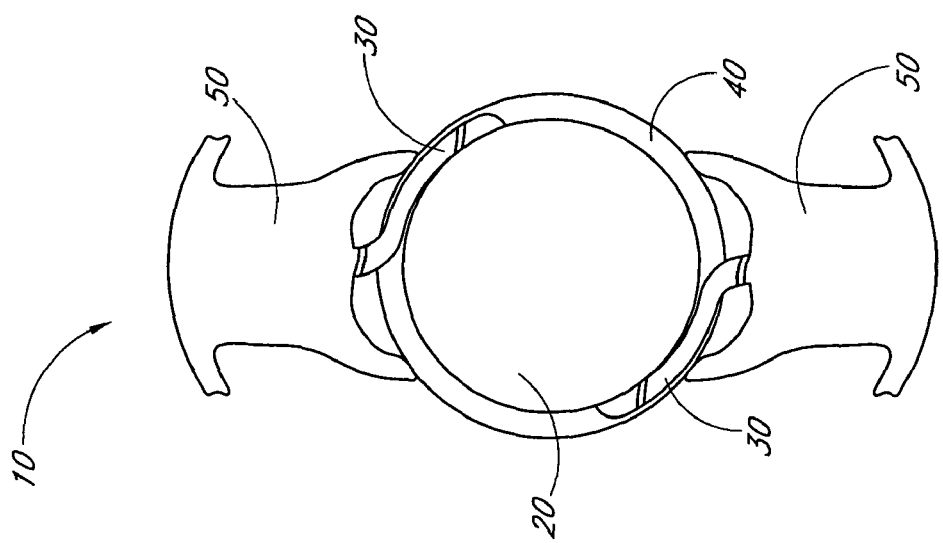
FIG. 10 schematically illustrates an embodiment of the intraocular lens system utilizing an anterior haptic arm and a posterior haptic member which form an integral unit.

FIG. 10 schematically illustrates an embodiment of the intraocular lens system 10 utilizing an anterior haptic arm 30 and a posterior haptic member 50 which form an integral unit (e.g., a single piece serves as both components). In certain such embodiments, the anterior haptic arm 30 is an extension from the posterior haptic member 50. In other embodiments, the posterior haptic member 50 is an extension from the anterior haptic arm 30. Such embodiments can provide a capability for more precise manufacturing of the intraocular lens system 10.

Figure 11:
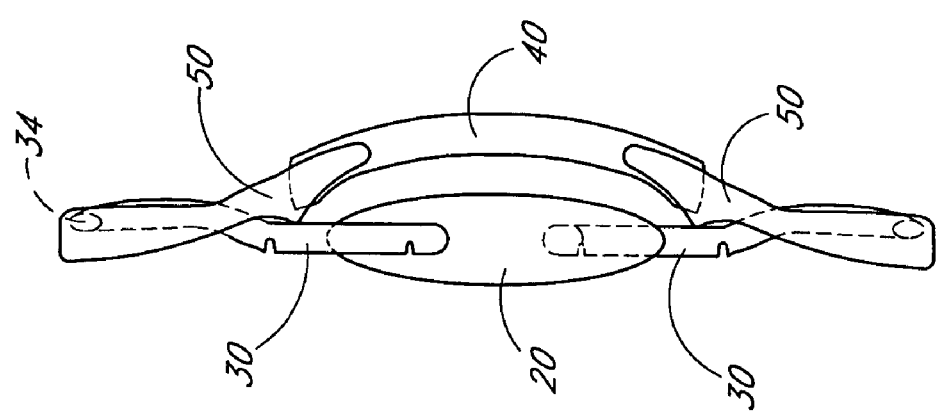
FIG. 11 schematically illustrates an embodiment of the intraocular lens system in which the posterior haptic member is coupled to the anterior haptic arm.

FIG. 11 schematically illustrates an embodiment of the intraocular lens system 10 in which the posterior haptic member 50 is coupled to the anterior haptic arm 30. In certain such embodiments, movement of the posterior haptic member 50, rather than movement of the posterior optic 40, deflects the anterior haptic arms 30 so as to move the anterior optic 20 in the forward direction. Such embodiments can provide a capability for larger movement amplification factors.

Various embodiments of the present invention have been described above. Although this invention has been described with reference to these specific embodiments, the descriptions are intended to be illustrative of the present invention and are not intended to be limiting. In particular, components, features, or other aspects of the various embodiments described herein can be combined or interchanged with one another in any desirable order, amount, arrangement, or configuration. Various modifications and applications may occur to those skilled in the art without departing from the true spirit and scope of the present invention as defined in the appended claims.

What is claimed is:

1. An intraocular lens system adapted to be implanted within an eye, the intraocular lens system comprising:
    an anterior optic movable in a forward direction within the eye;
    at least two anterior haptic arms extending radially outward from the anterior optic, each anterior haptic arm having a first end coupled to the anterior optic and a second end adapted to be coupled to the eye;
    a posterior optic movable in the forward direction within the eye and coupled to the anterior haptic arms, wherein the posterior optic contacts the at least two anterior haptic arms inward of the second end of each anterior haptic arm towards the anterior optic; and
    at least one posterior haptic member adapted to be coupled to the eye and coupled to the posterior optic, wherein the anterior haptic arms are responsive to a first forward movement of the posterior optic by actuating a second forward movement of the anterior optic, the second forward movement substantially larger than the first forward movement.

2. The intraocular lens system of claim 1, wherein the second end of each anterior haptic arm is adapted to be coupled to the capsular bag of the eye.

3. The intraocular lens system of claim 1, wherein the posterior haptic member is adapted to be coupled to the capsular bag of the eye.

4. The intraocular lens system of claim 1, wherein the second end of each anterior haptic arm is adapted to be coupled to the zonular fibers of the eye.

5. The intraocular lens system of claim 1, wherein the posterior haptic member is adapted to be coupled to the zonular fibers of the eye.

6. The intraocular lens system of claim 1, wherein the anterior optic and the posterior optic are movable within the capsular bag of the eye.

7. The intraocular lens system of claim 1, wherein the posterior optic comprises an edge, wherein the edge engages at least one anterior haptic arm.

8. The intraocular lens system of claim 1, wherein the posterior optic comprises at least two grooves, wherein each groove engages at least one anterior haptic arm.

9. The intraocular lens system of claim 1, wherein the anterior optic rotates about an axis in response to the first forward movement of the posterior optic.

10. The intraocular lens system of claim 1, wherein the first forward movement and the second forward movement result in a change of power of the intraocular lens system of between approximately 10 diopters and approximately 30 diopters.

11. The intraocular lens system of claim 1, wherein the first forward movement and the second forward movement result in a change of power of the intraocular lens system of approximately 20 diopters.

12. The intraocular lens system of claim 1, comprising a pair of posterior haptic members positioned substantially symmetrically to the posterior optic.

* * * * *

UNITED STATES PATENT AND TRADEMARK OFFICE
CERTIFICATE OF CORRECTION

PATENT NO. : 7,238,201 B2
APPLICATION NO. : 10/635423
DATED : July 3, 2007
INVENTOR(S) : Portney et al.

It is certified that error appears in the above-identified patent and that said Letters Patent is hereby corrected as shown below:

Title Page at column 2, (Other Publications), line 3, please delete "Ophthalmolgoy" and insert -- Ophthalmology --, therefor.

Page 2 at column 1, (U.S. Patent Documents), line 12, please delete "Weinschen" and insert -- Weinschenk --, therefor.

Page 2 at column 2, (Other Publications), line 8, please delete "Placemnent" and insert -- Placement --, therefor.

At column 1, line 39, please delete "experienced" and insert -- experience --, therefor.

At column 5, line 15, please delete "glue,." and insert -- glue, --, therefor.

Signed and Sealed this

Twenty-fifth Day of March, 2008

JON W. DUDAS
*Director of the United States Patent and Trademark Office*